(12) United States Patent
Kassem

(10) Patent No.: US 7,842,004 B2
(45) Date of Patent: Nov. 30, 2010

(54) WIRELESS PRESSURE SETTING INDICATOR

(75) Inventor: Salim Kassem, North Attleboro, MA (US)

(73) Assignee: Codman & Shurtleff, Inc., Raynham, MA (US)

( * ) Notice: Subject to any disclaimer, the term of this patent is extended or adjusted under 35 U.S.C. 154(b) by 207 days.

(21) Appl. No.: 11/931,041

(22) Filed: Oct. 31, 2007

(65) Prior Publication Data

US 2009/0112147 A1    Apr. 30, 2009

(51) Int. Cl.
*A61M 5/00* (2006.01)

(52) U.S. Cl. .......................................... 604/9

(58) Field of Classification Search ............... 604/6.16, 604/9, 7, 8, 10; 137/530, 531; 251/65, 177, 251/228
See application file for complete search history.

(56) References Cited

U.S. PATENT DOCUMENTS

| | | |
|---|---|---|
| 2,396,351 A | 3/1946 | Thompson |
| 3,886,948 A | 6/1975 | Hakim et al. |
| 3,960,142 A | 6/1976 | Elliott et al. |
| 3,976,278 A | 8/1976 | Dye et al. |
| 4,077,882 A | 3/1978 | Gangemi |
| 4,114,603 A | 9/1978 | Wilkinson |
| 4,127,110 A | 11/1978 | Bullara |
| 4,135,509 A | 1/1979 | Shannon |
| 4,237,900 A | 12/1980 | Schulman et al. |
| 4,332,255 A | 6/1982 | Hakim et al. |
| 4,385,636 A | 5/1983 | Cosman |

(Continued)

FOREIGN PATENT DOCUMENTS

AU    729467    2/2001

(Continued)

OTHER PUBLICATIONS

Ekstedt, J., "CSFS Hydrodynamic Studies in Man, 1. Method of Constant Pressure CSF Infusion," J. Neurology, Neurosurgery & Psych.40:105-19 (1977).

(Continued)

*Primary Examiner*—Tatyana Zalukaeva
*Assistant Examiner*—Benedict L Hanrahan
(74) *Attorney, Agent, or Firm*—Nutter McClennen & Fish LLP

(57) ABSTRACT

Devices and methods useful for non-invasively indicating the position or setting of a mechanical device, such as a sensor or control in an implanted medical device, are disclosed. In one exemplary embodiment, a valve housing adapted to receive fluid flow therethrough is provided. The flow of fluid through the valve housing can be controlled, for example, by a valve assembly that has a plurality of predetermined pressure settings. A radio frequency tag can be disposed in the valve assembly, and the masking element and the radio frequency tag can be configured to move relative to one another. The relative positions of the masking element and the radio frequency tag can alter the response of the radio frequency tag to a wireless signal (which can be emitted from an external reading device, for example) and thereby indicate the pressure setting of the valve assembly. For example, in some embodiments, the masking element can selectively cover at least part of the radio frequency tag according to the pressure setting of the valve assembly, which can change a characteristic of the radio frequency tag's response to the wireless signal.

19 Claims, 13 Drawing Sheets

U.S. PATENT DOCUMENTS

| | | |
|---|---|---|
| 4,387,715 A | 6/1983 | Hakim et al. |
| 4,421,124 A | 12/1983 | Marshall |
| 4,494,950 A | 1/1985 | Fischell |
| 4,540,400 A * | 9/1985 | Hooven ............... 604/9 |
| 4,551,128 A | 11/1985 | Hakim et al. |
| 4,556,086 A | 12/1985 | Raines |
| 4,576,181 A | 3/1986 | Wallace et al. |
| 4,593,703 A | 6/1986 | Cosman |
| 4,595,390 A | 6/1986 | Hakim et al. |
| 4,611,578 A | 9/1986 | Heimes et al. |
| 4,615,691 A | 10/1986 | Hakim et al. |
| 4,625,730 A | 12/1986 | Fountain et al. |
| 4,660,568 A * | 4/1987 | Cosman ............... 600/561 |
| 4,676,772 A | 6/1987 | Hooven |
| 4,711,249 A | 12/1987 | Brooks |
| 4,718,425 A | 1/1988 | Tanaka et al. |
| 4,723,556 A | 2/1988 | Sussman |
| 4,727,887 A | 3/1988 | Haber |
| 4,772,257 A * | 9/1988 | Hakim et al. ............ 604/9 |
| 4,785,822 A | 11/1988 | Wallace |
| 4,787,886 A * | 11/1988 | Cosman ............... 604/9 |
| 4,820,265 A | 4/1989 | DeSatnick et al. |
| 4,841,977 A | 6/1989 | Griffith et al. |
| 4,850,358 A | 7/1989 | Millar |
| 4,885,002 A | 12/1989 | Watanabe et al. |
| 4,893,630 A | 1/1990 | Bray, Jr. |
| 5,004,472 A | 4/1991 | Wallace |
| 5,009,662 A | 4/1991 | Wallace et al. |
| 5,021,046 A | 6/1991 | Wallace |
| 5,163,904 A | 11/1992 | Lampropoulos et al. |
| 5,201,753 A | 4/1993 | Lampropoulos et al. |
| 5,252,962 A | 10/1993 | Urbas et al. |
| 5,265,606 A | 11/1993 | Kujawski |
| 5,280,789 A | 1/1994 | Potts |
| 5,321,989 A | 6/1994 | Zimmer et al. |
| 5,337,612 A | 8/1994 | Evans |
| 5,385,514 A | 1/1995 | Dawe |
| 5,396,899 A | 3/1995 | Strittmatter |
| 5,417,235 A | 5/1995 | Wise et al. |
| 5,425,713 A | 6/1995 | Taylor et al. |
| 5,431,057 A | 7/1995 | Zimmer et al. |
| 5,431,629 A | 7/1995 | Lampropoulos et al. |
| 5,449,345 A | 9/1995 | Taylor et al. |
| 5,490,514 A | 2/1996 | Rosenberg |
| 5,591,171 A | 1/1997 | Brown |
| 5,622,869 A | 4/1997 | Lewis et al. |
| 5,630,836 A | 5/1997 | Prem et al. |
| 5,643,194 A * | 7/1997 | Negre ............... 604/8 |
| 5,704,352 A | 1/1998 | Tremblay et al. |
| 5,711,302 A | 1/1998 | Lampropoulos et al. |
| 5,716,342 A | 2/1998 | Dumbraveanu et al. |
| 5,721,382 A | 2/1998 | Kriesel et al. |
| 5,797,403 A | 8/1998 | DiLorenzo |
| 5,803,917 A | 9/1998 | Butterfield et al. |
| 5,836,886 A | 11/1998 | Itoigawa et al. |
| 5,873,840 A | 2/1999 | Neff |
| 5,928,182 A * | 7/1999 | Kraus et al. ............ 604/9 |
| 5,935,083 A | 8/1999 | Williams |
| 5,970,801 A | 10/1999 | Ciobanu et al. |
| 5,993,395 A | 11/1999 | Shulze |
| 5,993,398 A | 11/1999 | Alperin |
| 6,010,482 A | 1/2000 | Kriesel et al. |
| 6,025,725 A | 2/2000 | Gershenfeld et al. |
| 6,071,267 A | 6/2000 | Zamierowski |
| 6,083,174 A | 7/2000 | Brehmeier-Flick et al. |
| 6,111,520 A | 8/2000 | Allen et al. |
| 6,113,553 A | 9/2000 | Chubbuck |
| 6,120,457 A | 9/2000 | Coombes et al. |
| 6,158,965 A | 12/2000 | Butterfield et al. |
| 6,171,252 B1 | 1/2001 | Roberts |
| 6,208,254 B1 | 3/2001 | McQueen et al. |
| 6,248,080 B1 | 6/2001 | Miesel et al. |
| 6,264,612 B1 | 7/2001 | McConnell et al. |
| 6,278,379 B1 | 8/2001 | Allen et al. |
| 6,316,522 B1 | 11/2001 | Loomis et al. |
| 6,371,976 B1 | 4/2002 | Vrzalik et al. |
| 6,416,291 B1 | 7/2002 | Butterfield et al. |
| 6,439,538 B1 * | 8/2002 | Ito ............... 251/65 |
| 6,470,213 B1 | 10/2002 | Alley |
| 6,481,292 B1 | 11/2002 | Reich |
| 6,503,208 B1 | 1/2003 | Skovlund et al. |
| 6,533,733 B1 | 3/2003 | Ericson et al. |
| 6,537,232 B1 | 3/2003 | Kucharczyk et al. |
| 6,589,189 B2 | 7/2003 | Meyerson et al. |
| 6,626,902 B1 | 9/2003 | Kucharczyk et al. |
| 6,636,769 B2 | 10/2003 | Govari et al. |
| 6,682,490 B2 | 1/2004 | Roy et al. |
| 6,724,310 B1 | 4/2004 | Gershenfeld et al. |
| 6,731,976 B2 | 5/2004 | Penn et al. |
| 6,770,030 B1 | 8/2004 | Schaupp et al. |
| 6,855,115 B2 | 2/2005 | Fonseca et al. |
| 6,891,474 B1 | 5/2005 | Fletcher |
| 7,435,229 B2 | 10/2008 | Wolf |
| 2002/0035331 A1 | 3/2002 | Brockway et al. |
| 2002/0052563 A1 | 5/2002 | Penn et al. |
| 2002/0077553 A1 | 6/2002 | Govari et al. |
| 2002/0087059 A1 | 7/2002 | O'keefe |
| 2002/0099428 A1 | 7/2002 | Kaufman |
| 2003/0023134 A1 | 1/2003 | Tracey |
| 2003/0032915 A1 | 2/2003 | Saul |
| 2003/0135110 A1 | 7/2003 | Leussler |
| 2003/0216666 A1 | 11/2003 | Ericson et al. |
| 2004/0073137 A1 | 4/2004 | Lloyd et al. |
| 2004/0134991 A1 | 7/2004 | Fletcher et al. |
| 2004/0147871 A1 | 7/2004 | Burnett |
| 2004/0193021 A1 | 9/2004 | Zdeblick et al. |
| 2005/0043669 A1 | 2/2005 | Rosenberg |
| 2005/0043670 A1 | 2/2005 | Rosenberg |
| 2005/0165317 A1 | 7/2005 | Turner et al. |
| 2005/0187487 A1 | 8/2005 | Azizkhan et al. |
| 2005/0197585 A1 | 9/2005 | Brockway et al. |
| 2005/0277839 A1 | 12/2005 | Alderman et al. |
| 2006/0009699 A1 | 1/2006 | Roteliuk et al. |
| 2006/0020239 A1 | 1/2006 | Geiger et al. |
| 2006/0036208 A1 | 2/2006 | Burnett |
| 2006/0149161 A1 | 7/2006 | Wilson et al. |
| 2006/0189888 A1 | 8/2006 | Hassler et al. |
| 2006/0211944 A1 | 9/2006 | Mauge et al. |
| 2006/0211945 A1 | 9/2006 | Mauge et al. |
| 2006/0211946 A1 * | 9/2006 | Mauge et al. ............ 600/488 |
| 2007/0167867 A1 | 7/2007 | Wolf |
| 2008/0139959 A1 | 6/2008 | Miethke et al. |
| 2009/0107233 A1 | 4/2009 | Kassem |
| 2009/0112103 A1 | 4/2009 | Kassem |
| 2009/0112308 A1 | 4/2009 | Kassem |
| 2010/0168673 A1 | 7/2010 | Stergiopulos et al. |

FOREIGN PATENT DOCUMENTS

| | | |
|---|---|---|
| CN | 2555770 Y | 6/2003 |
| DE | 4042335 | 8/1991 |
| DE | 4042336 | 8/1991 |
| EP | 0115548 | 8/1984 |
| EP | 0619101 | 10/1994 |
| EP | 1312302 | 5/2003 |
| EP | 1389477 | 2/2004 |
| EP | 1491137 | 12/2004 |
| EP | 1738792 A1 | 1/2007 |
| JP | 2003821 A | 1/1990 |
| WO | WO-9105575 | 5/1991 |
| WO | WO-9953990 A1 | 10/1999 |
| WO | 0121066 A1 | 3/2001 |
| WO | 2005046467 A1 | 5/2005 |
| WO | 2006048664 | 5/2006 |

| | | |
|---|---|---|
| WO | WO-2006117123 | 11/2006 |
| WO | 2007041843 A1 | 4/2007 |
| WO | 2007081741 | 7/2007 |

OTHER PUBLICATIONS

European Search Report, Appl. No. 052580800.0, dated May 15, 2006.

Shapiro, K. et al. "Characterization of Clinical CSF Dynamics and Neural Zxis Compliance Using the Pressure-Volume Index: 1. The Normal Pressure-Volume Index," Annals of Neurology, 7(6):508-14 (1980).

"User's Manual HD2114.0-HD2134.0, HD2164.0-HD2114B.0, HD2114, 2-HD2134.2, HD2164.2-HD2114B.2; Rev. 1.0," Delta OHM, Via g. Marconi, 5-35020 Caselle Di Selvazzano (PD)—Italy, pp. 2-6 (2004).

Dobkin et al., "A Radio-Oriented Introduction to RFID-Protocols, Tags and Applications," High Frequency Electronics, 32-46 (2005).

European Search Report, EP Application No. 08253554, Mailed Feb. 19, 2009.

Ko et al: "Cerebrospinal Fluid Control System," Proceeding of the IEEE, IEEE. New York, US, vol. 76, No. 9, Sep. 1, 1988, pp. 1226-1235, XP000094517 ISSN: 0018-9219.

European Search Report, EP Application No. 08253545.1-1526, mailed Mar. 5, 2009.

J.S. Kroin, et al., "Long-term testing of an intracranial pressure monitoring device", J. Neurosurg, V. 93, pp. 852-858, 2000.

"Sensor Transponder for Pressure and Temperature", data sheet of Institut Mikroelektronische Schaultungen und Systeme, pp. 1-2, Feb. 2000.

"Telemetric Integrated Pressure Sensors", product data sheet of Institut Mikroelektronische Schaultungen und Systeme, p. 1, Sep. 2002.

"Surface Micromachined Pressure Sensor Technologies", product data sheet of Institut Mikroelektronische Schaultungen und Systeme, pp. 1-2, Sep. 2002.

U.S. Office Action for U.S. Appl. No. 11/931,187 dated May 11, 2010, 8 pages.

U.S. Office Action for U.S. Appl. No. 11/931,187 dated Oct. 6, 2010, 8 pages.

* cited by examiner

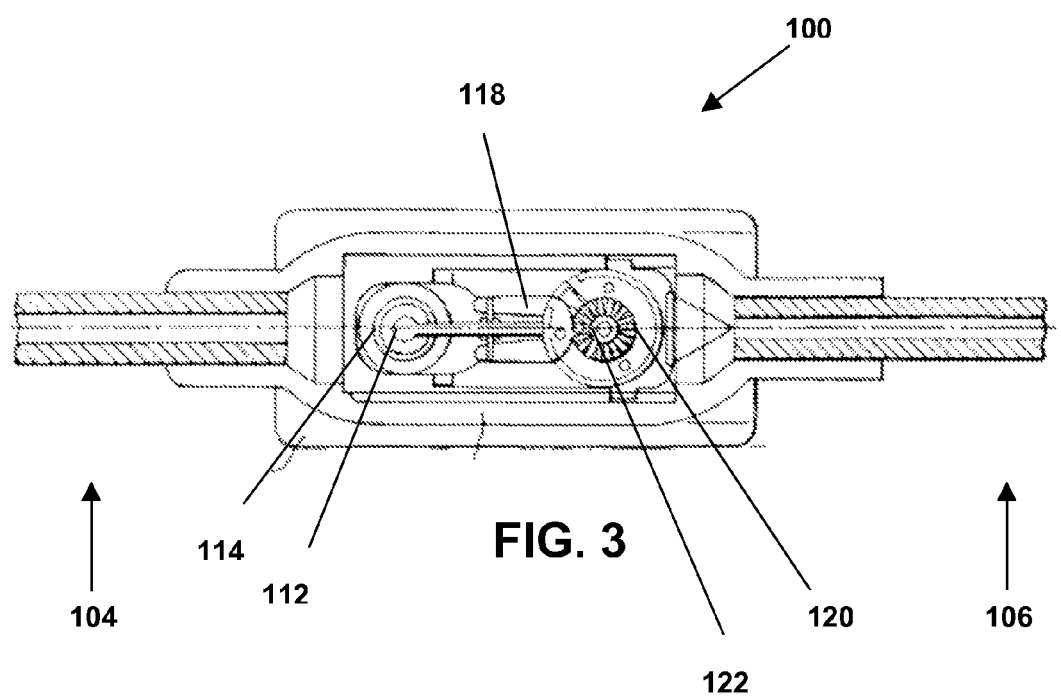

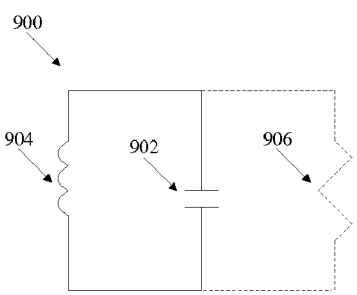
FIG. 9A
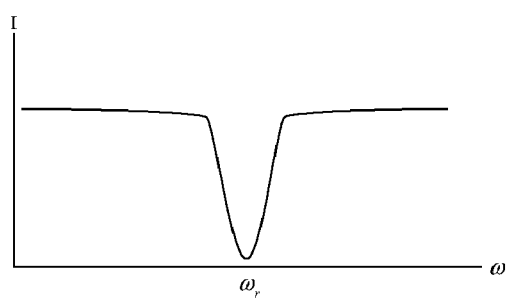 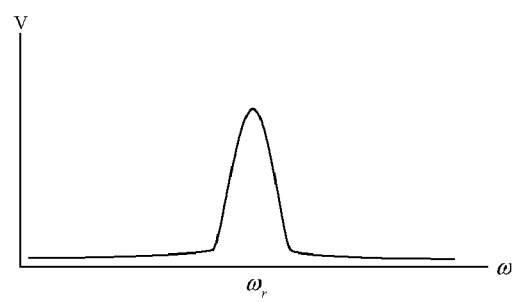
FIG. 9B  FIG. 9C

1000

WIRELESS PRESSURE SETTING INDICATOR

FIELD

The present application generally relates to devices and methods for non-invasively indicating the position or setting of a mechanical device, and more particularly for indicating a setting in an implantable medical device, such as the pressure setting in a wireless shunt.

BACKGROUND

It is often desirable to non-invasively determine the position or setting of a mechanical device, such as a switch, valve, pressure setting mechanism, or other sensor or control, and to be able to indicate the setting to a remote device.

By way of illustration, treatment of hydrocephalus can involve selecting a pressure setting on an implantable valve to control the flow of cerebrospinal fluid through a hydrocephalus shunt. Hydrocephalus is a neurological condition that is caused by the abnormal accumulation of cerebrospinal fluid (CSF) within the ventricles, or cavities, of the brain. CSF is a clear, colorless fluid that is primarily produced by the choroid plexus and surrounds the brain and spinal cord, aiding in their protection. Hydrocephalus can arise when the normal drainage of CSF in the brain is blocked in some way, which creates an imbalance between the amount of CSF produced by the choroid plexus and the rate at which CSF is absorbed into the bloodstream, thereby increasing pressure on the brain.

Hydrocephalus is most often treated by surgically implanting a shunt system in a patient. The shunt system diverts the flow of CSF from the ventricle to another area of the body where the CSF can be absorbed as part of the circulatory system. Shunt systems come in a variety of models and typically share similar functional components. These components include a ventricular catheter, which is introduced through a burr hole in the skull and implanted in the patient's ventricle, a drainage catheter that carries the CSF to its ultimate drainage site, and optionally a flow-control mechanism, e.g., shunt valve, that regulates the one-way flow of CSF from the ventricle to the drainage site to maintain normal pressure within the ventricles. The shunt valve can have several settings which determine the pressure at which it will allow CSF to flow the ventricular catheter to the drainage catheter. It is this pressure setting, which can correspond to the position of components in the valve, that may need to be determined.

In some cases, determining the pressure setting of a shunt valve can be accomplished using X-rays, magnetic tools, and/or using acoustic feedback. However, it would be advantageous to provide a pressure setting indicator that offers more accurate information directly from the shunt valve, instantaneously and without the need for radiation or cumbersome instruments. Such considerations can apply to a wide range of applications involving settings for implanted or embedded controls, valves, switches, and so on, both in medical devices and elsewhere.

Accordingly, there remains a need for non-invasively indicating the position or setting of a mechanical device, particularly in implanted medical devices.

SUMMARY

In one embodiment, an implantable valve is provided. The implantable valve can include a valve housing that has a valve inlet and a valve outlet, and that is adapted to receive fluid flow therethrough. The valve housing can have a valve assembly for controlling the rate of fluid flowing through the valve housing. The valve assembly can have a plurality of predetermined pressure settings for controlling the fluid flow. The implantable valve can also include a device that interacts with a wireless signal (for example, an electromagnetic wireless interrogation signal). For example, the implantable valve can include a radio frequency tag that interacts with a wireless signal emitted by an external reader. The radio frequency tag can produce a response to the wireless signal. A masking element can be disposed in the valve housing, and the masking element and the radio frequency tag can be configured to move relative to one another (for example, the masking element can move relative to the radio frequency tag, or vice versa) to alter the response of the radio frequency tag and thereby indicate a pressure setting of the valve assembly. The masking element, for example, can include a conductive member, for example an electrically conductive material, that alters the response of the radio frequency tag by covering at least a portion of it. The conductive member can influence one or several characteristics of the radio frequency tag. For example, the response of the radio frequency tag can have one or more characteristics, such as a resonant frequency, harmonic spectra, decay characteristic, and Q factor. One or more of the characteristics can indicate the pressure setting. In some embodiments, a sensor can be disposed within the valve housing and it can measure the pressure of fluid in the valve housing.

The valve assembly can also include an adjustment mechanism that is configured to move (for example, it can rotate) to select a pressure setting. The linear or angular movement can also cause the masking element to move, for example, relative to the radio frequency tag. The valve assembly can also include a movable adjustment mechanism that selects a pressure setting in response to a magnetic field created by an external control device.

The radio frequency tag can have a variety of configurations. For example, the radio frequency tag can include a disk that has an asymmetrical antenna formed on it, and the masking element can be configured to at least partially mask the antenna. In some embodiments, the radio frequency tag can include a chip for storing data and an antenna adapted to communicate the stored data to an external reading device.

The masking element can also have a variety of configurations. For example, the masking element can include a disk formed at least in part of a conductive material and configured to rotate around an axis thereof such that the conductive material selectively masks at least part of the radio frequency tag. In some embodiments, the conductive material can be in the form of a spiral or a plurality of discrete conductive sections, each of which can be formed on the disk. In other embodiments, the masking element can be a wedge formed at least in part of a conductive material. For example, the valve assembly can have a movable adjustment mechanism configured to select a pressure setting and to cause the masking element to move, which can result in lateral movement of the wedge.

In another embodiment, an implantable valve is provided which has a valve inlet and a valve outlet that are adapted to receive fluid flow therethrough, and which also has a valve assembly for controlling the rate of fluid flowing through the valve housing. The valve assembly can have a plurality of predetermined pressure settings for controlling the fluid flow. The implantable valve can also have a conductive member disposed within the valve assembly that is configured to selectively cover at least a portion of a radio frequency tag, for example depending on the pressure setting, and thereby alter the response of the radio frequency tag to indicate the selected pressure setting. The response can have at least one measurable characteristic, such as resonance frequency, harmonic spectra, decay characteristic, and Q factor, which for example can indicate the selected pressure setting. The radio frequency tag can produce the response when interrogated by a wireless signal emitted from an external reading device. In some embodiments, the radio frequency tag can include a chip for storing data and an antenna adapted to communicate the stored data to such an external reading device.

The radio frequency tag can be configured to move relative to the conductive member, for example, such that at least a portion of the radio frequency tag is covered by the conductive material. In some embodiments, the radio frequency tag can include a disk having an asymmetrical antenna formed thereon.

The conductive member can also be configured to move relative to the radio frequency tag, for example, such that at least a portion of the radio frequency tag is covered by the conductive member. The conductive member can form part of a rotatable disk, and/or the conductive member can be in the form of a layer (on the disk, for example) in the shape of, for example, a spiral or a plurality of discrete conductive sections.

In yet another exemplary embodiment, an implantable valve can include a valve housing adapted to receive fluid flow therethrough between a valve inlet and a valve outlet, and a valve assembly disposed within the valve housing and having a plurality of selectable positions. The implantable valve can also include a radio frequency tag disposed in the valve housing and adapted to interact with a wireless signal to produce a response thereto, and can include a masking element disposed in the valve housing. The masking element and the radio frequency tag can be configured to move relative to one another to alter the response of the radio frequency tag and thereby indicate the selected position of the valve assembly.

In other aspects, methods for indicating the pressure setting of an implanted valve are provided. In one embodiment, an exemplary method includes transmitting a wireless signal from a reading device to the radio frequency tag disposed within a valve housing positioned between an inlet tube and an outlet tube, and the radio frequency tag can be adapted to indicate a pressure setting of a valve disposed within the valve housing. In some embodiments, for example, the inlet tube can be coupled to a catheter within a patient's ventricle, and the outlet tube can be coupled to a drainage catheter for draining the patient's cerebrospinal fluid. The valve housing can also be coupled to a sensor assembly that is adapted to measure a pressure of fluid within the valve housing. The valve housing can have a radio frequency tag disposed therein, and the valve housing can be adapted to control a rate of fluid flowing therethrough according to a pressure setting selected from the plurality of pressure settings. The method can further include wirelessly receiving a response to the wireless signal from the radio frequency tag that indicates the current pressure setting. In some embodiments, the response from the radio frequency tag can communicate information previously stored therein.

The method can further include changing the pressure setting of the valve to a second pressure setting, and wirelessly receiving a second response from the radio frequency tag that indicates the second pressure setting. The selection of one of the plurality of pressure settings can be performed, for example, with an external control device adapted to emit a magnetic field. The method can also include analyzing the response from the radio frequency tag to detect any of resonant frequency, harmonic spectra, decay characteristics, and Q factor.

BRIEF DESCRIPTION OF THE DRAWINGS

Various exemplary embodiments disclosed herein will be more fully understood from the following detailed description taken in conjunction with the accompanying drawings, in which:

FIG. 3 is a top cutaway view of the valve shown in FIG. 2;

FIG. 9A is a schematic diagram of one exemplary model of a circuit having resonance characteristics;

FIG. 9B is a graph of an output voltage signal as a function of frequency for the circuit shown in FIG. 9A;

FIG. 9C is a graph of an output voltage signal as a function of frequency for the circuit shown in FIG. 9A;

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope is defined solely by the claims. The features illustrated or described in connection with one exemplary embodiment may be combined with the features of other embodiments. Such modifications and variations are intended to be included within the scope of the present application.

The present application generally provides methods and devices for non-invasively indicating the position or setting of a mechanical device, such as a mechanical control, and for indicating that information to another device, e.g., using telemetry. The methods and devices are particularly useful in the context of implantable devices, such as hydrocephalus shunts and associated valves. While the description herein sometimes refers to hydrocephalus shunts, such description is by way of illustration only. The devices and methods described herein can be used to indicate the settings and/or positions of a wide variety of controls, including valves, switches, and so on, both in and out of the context of hydrocephalus shunts. They can also be used to indicate the settings and/or positions of sensors that may adopt a particular position in response to a physical or environmental stimulus. The devices and methods provided herein can be used in a range of medical devices and in virtually any medical procedure now or later in use.

Figure 1:
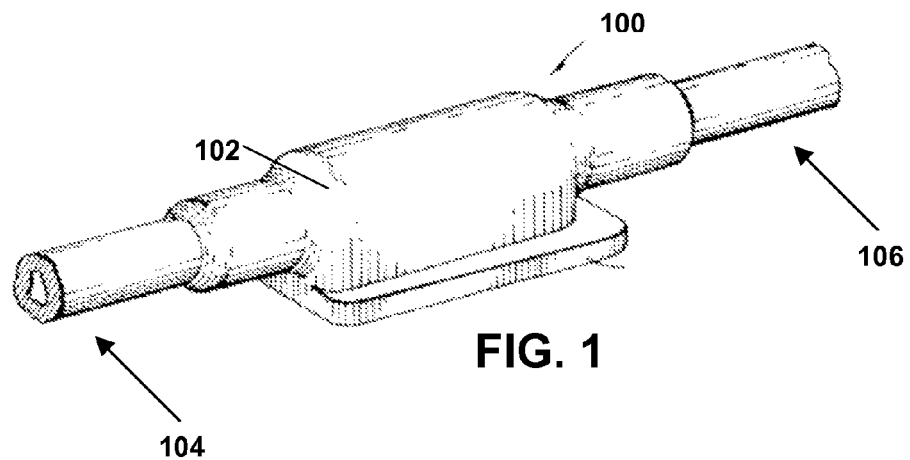
FIG. 1 is a perspective view of one exemplary embodiment of an implantable valve.
Figure 2:
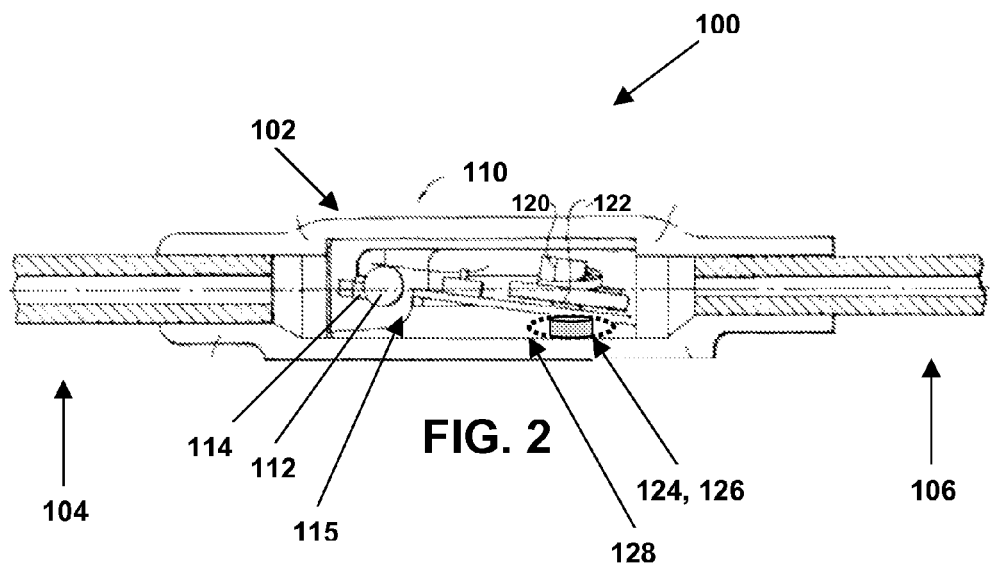
FIG. 2 is a side cutaway view of the valve shown in FIG. 1 showing a radio frequency tag and a masking element.

FIGS. 1-3 illustrate one exemplary embodiment of an implantable valve 100 having a housing 102 for receiving fluid flow between a valve inlet 104 and an valve outlet 106. The housing 102 can have virtually any configuration, shape, and size. In many embodiments, the size and shape of the housing 102 can be adapted for implantation in a body, e.g., subcutaneous implantation. In the embodiment shown in FIGS. 1-3, the housing 102 has a substantially linear configuration. In other embodiments, the housing can include and/or define a reservoir having a larger area than the ports 106, 110, which can be advantageous for checking the shunt's patency, tapping the CSF, to administer therapy, or to house pressure or flow sensors.

The implantable valve 100 can include a valve assembly 110 for controlling the flow of fluid according to one of a plurality of selectable pressure settings. As shown, the valve assembly 110 includes a ball 112 engaging a valve seat 114, which sits in a valve opening 115 in the fluid path between the valve inlet 104 and the valve outlet 106, and which controls fluid flow therethrough. The ball 112 can be under the force of a spring 118 or other biasing element. The spring 118 can be in the form of an arm extending from an adjustment mechanism, which as shown in FIGS. 2 and 3 is a stepper motor 120, to the upper surface of the ball 112 such that it exerts a downward force thereon. The stepper motor 120 includes a stepped surface, each step representing a pressure setting. As can be seen in FIGS. 2-3, the rotational position of the stepper motor 120 can determine the force of the spring 118 on the ball 112 and thereby control the pressure at which fluid will flow through the valve opening 115. In use, the rotational position of the stepper motor 120 can be controlled by an external programmer, for example via a changing electromagnetic field applied to magnetic field elements disposed about a central axis 122 of the stepper motor 120 to rotate the stepper motor in a controlled fashion. The magnetic field elements can be magnets shaped and positioned with respect to the axis or rotor of the stepper motor 120. More information on the operation of stepper motors and such valves can be obtained from U.S. Pat. Nos. 5,928,182; 4,772,257; and 4,615,691, all of which are hereby incorporated by reference in their entireties.

The implantable valve 100 can also include a radio frequency (RF) tag 124 and a masking element 126 coupled to the stepper motor 120. (For clarity, the masking element 124 and RF tag 126 are represented together by an icon in FIG. 2, and embodiments thereof are shown in more detail in FIGS. 4-7.) As will be described in more detail below, the RF tag 124 and the masking element 126 can be configured to move relative to one another in response to and/or in relation to the rotation of the stepper motor 120 to indicate the current pressure setting of the valve 100 to an external reading device. In some embodiments, the RF tag 124 can include a chip capable of storing data, such as identification information (for the valve and/or for the patient) and pressure setting history, which can be communicated to the external reading device. The RF tag 124 and the masking element 126, as well as the valve 100, can include a coating 128 for protection from the external environment, CSF, and so on. The valve inlet 104 and valve outlet 106 can each be open and adapted to couple to another medical device, such as a ventricular catheter, drainage catheter, or other medical device. A person skilled in the art will appreciate that FIGS. 1-3 merely illustrate one exemplary embodiment of a valve for use with a radio frequency tag and masking element, and that various valves for controlling fluid flow known in the art can be used.

Figure 4A:
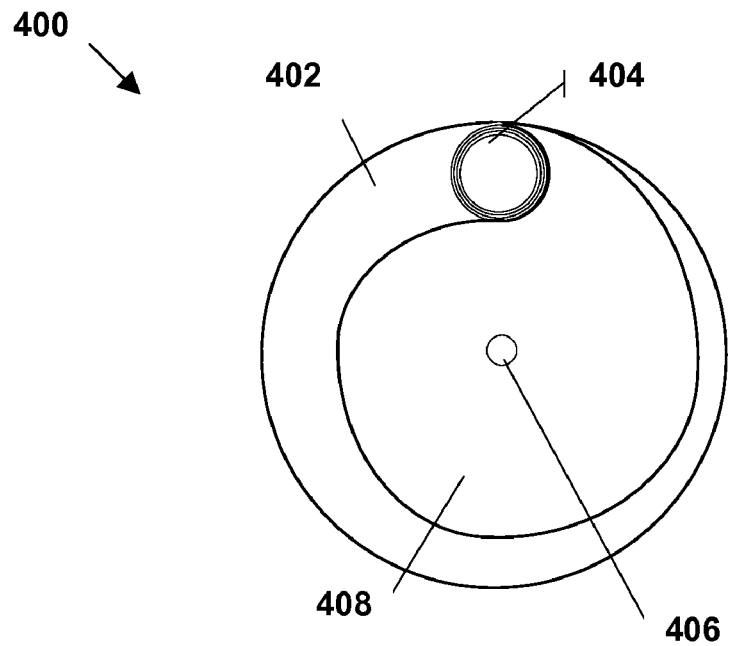
FIG. 4A is a top view of one exemplary embodiment of a radio frequency tag and a masking element.
Figure 4B:
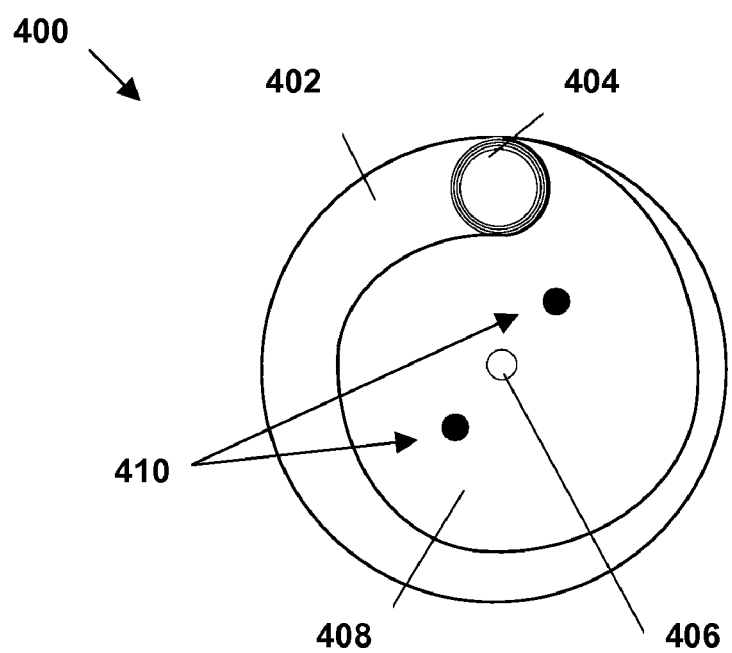
FIG. 4B is a top view of the masking element and radio frequency tag shown in FIG. 4A having magnetic field elements disposed thereon.

The masking element 126 can have a wide variety of configurations and it can be adapted to interact with the RF tag 124 in a variety of ways. In one exemplary embodiment shown in FIG. 4A, the masking element 400 can be in the form of a disk and can have an electrically conductive portion 402 and a non-conductive portion (or differently conductive) portion 408. The conductive portion 402 can be a material, such as silver, gold, copper, aluminum, or others known in the art, etc., deposited on the disk. The use of one or more magnetic portions is also possible. The conductive potion 402 can also be attached or coupled to the disk, or it can be a non-circular portion that fits together with a non-conductive portion 408 to form the complete disk, and so on. The conductive portion 402 can have a variety of shapes, but as shown it is spiral or C-shaped such that its width increases between concentric edges. Alternatively, the conductive portion 402 can be in the shape of a strip of varying width, and it can have virtually any shape that is rotationally asymmetric. As shown in FIG. 4A (and in more detail in FIG. 8, described below), the RF tag 404 can be disposed below (in other embodiments, it can be above) the masking element 400, and particularly below the spiral portion formed of conductive material 402. A small gap can separate the masking element 400 and the RF tag 404. In use, the rotational position of the stepper motor 120 can be communicated to the masking element 400 to effect rotation thereof about a central axis 406, while the RF tag 404 can remain fixed (for example, fixed relative to the valve 100 shown in FIGS. 1-3). Depending on the angular position of the masking element 404, the conductive material can cover a differing area of the RF tag 404. In some embodiments, the masking element 400 can include gears or be adapted to receive drive elements from the stepper motor 120 to effect rotation thereof. In other embodiments, the masking element 400 can include magnetic field elements, such as the magnets 410 shown in FIG. 4B, which are shaped and positioned to respond to a changing magnetic field from a programming device for the stepper motor 120, as previously mentioned. The masking element 400 can also be directly coupled to the stepper motor 120 such that it rotates with the motor. In other embodiments, in which the valve does not include a stepper motor, the masking element can be configured to move in coordination with whatever adjustment mechanism is used to alter the pressure setting of the valve.

Figure 4C:
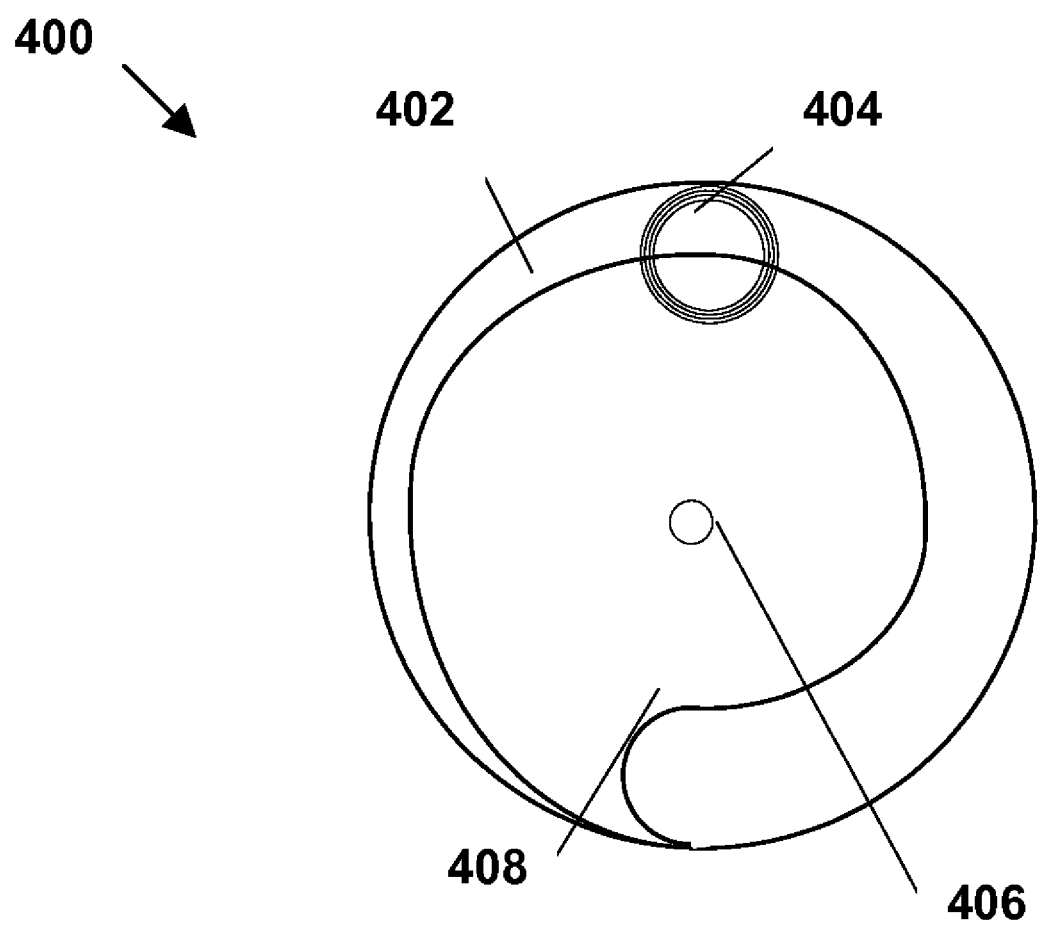
FIG. 4C is a top view the radio frequency tag and masking element of FIG. 4A following rotation of the masking element.

FIG. 4C illustrates one possible result of rotation of the masking element 400, in which, following rotation of the masking element 400 from the position shown in FIG. 4A, a narrow portion of the conductive material 402 covers the RF tag 404. Accordingly, the response of the RF tag 404 to an external signal (e.g., from a reading device emitting a signal at one or more radio frequencies) in FIG. 4C can differ from that of FIG. 4A to indicate such relative position and/or the fact that movement has occurred. For example, in some embodiments, a characteristic of the response of the RF tag 404, such as resonance frequency, harmonic spectra, or Q factor, can change depending on the relative position or motion of the masking element 400, indicating the position of the stepper motor and thus the pressure setting of the valve 100. In use, the external reading device can emit radio frequency signals across one or more frequencies and can analyze the responsive signal from the RF tag 402 for such a characteristic.

Figure 5A:
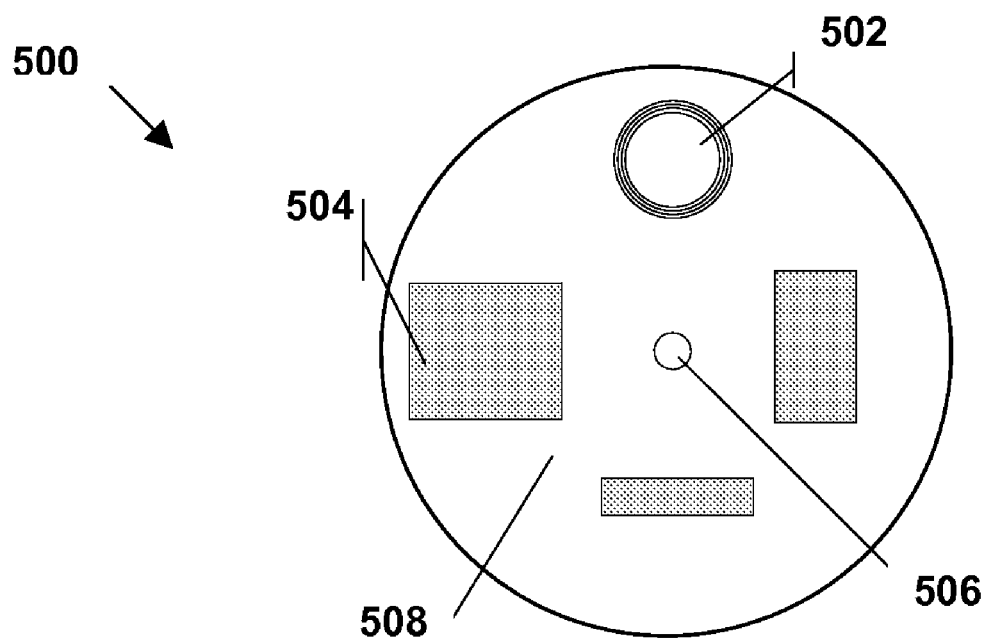
FIG. 5A is a top view of another embodiment of a radio frequency tag and a masking element.
Figure 5B:
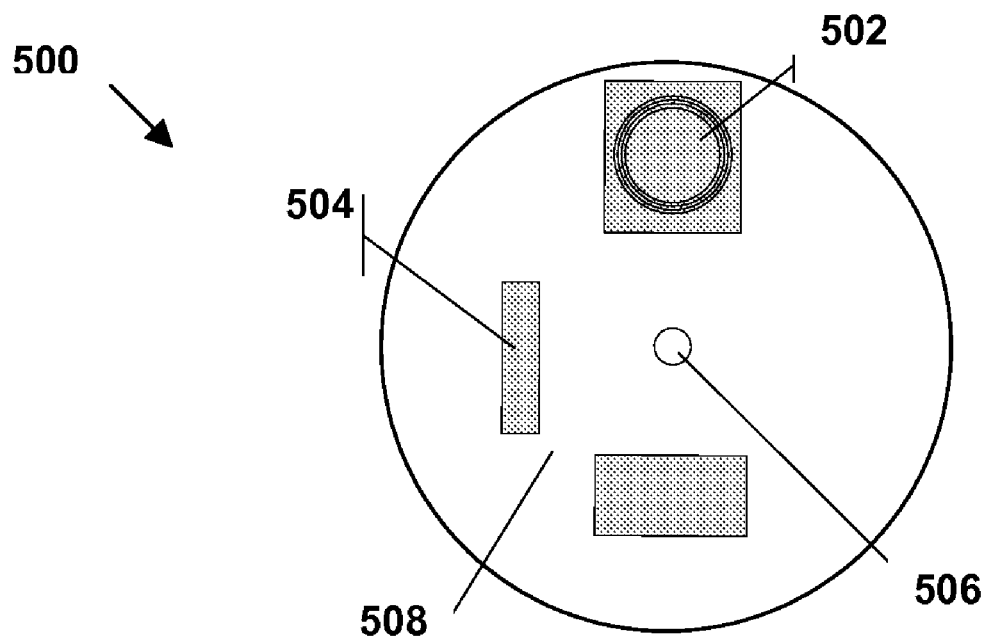
FIG. 5B is a top view the radio frequency tag and masking element shown in FIG. 5A following rotation of the masking element.
Figure 5C:
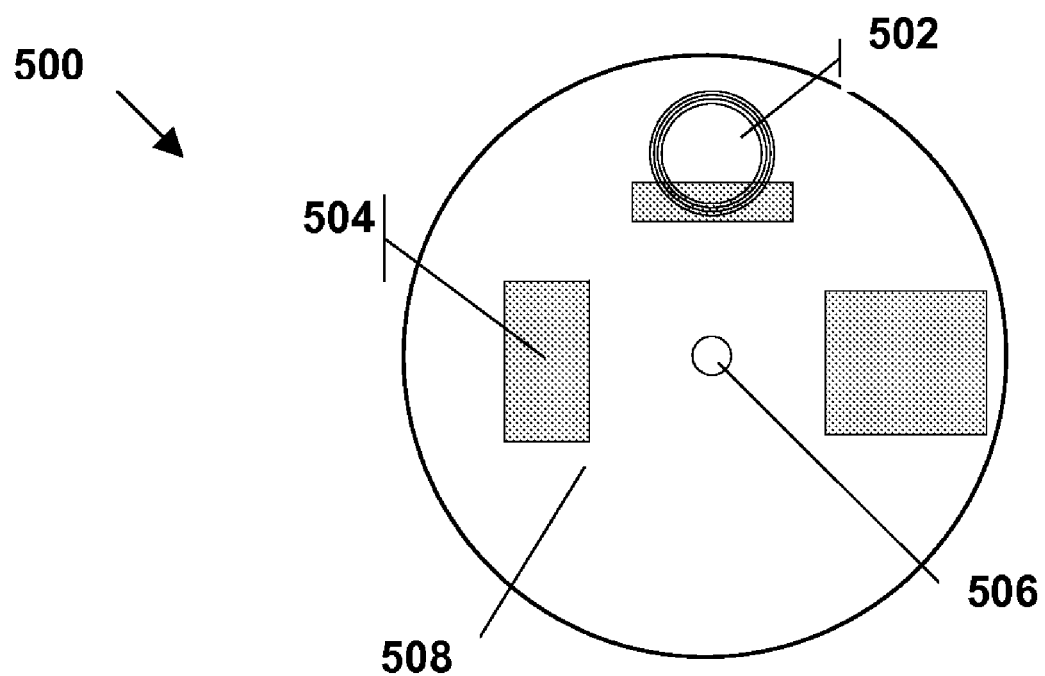
FIG. 5C is a top view the radio frequency tag and masking element shown in FIG. 5A following rotation of the masking element.

The masking element and the RF tag can have a wide variety of other configurations. For example, FIG. 5A illustrates another exemplary masking element 500 which has a plurality of discrete conductive portions 504 disposed within a disk 508 of non-conductive material 508. As shown, the conductive portions 504 are rectangular and vary in shape and size; however the conductive portions 504 can be virtually any size and shape and in some embodiments can be identical. Some of the conductive portions 504 can be sized to completely cover the RF tag 502, while other conductive portions 504 can be sized to partially cover the RF tag 502. The masking element 500 can be adapted to rotate around an axis 506 (for example, via coupling to the stepper motor 120 of FIG. 2, which coupling may include gears or other elements to transfer mechanical force). FIGS. 5B and 5C illustrate two possible positions of the masking element 500 relative to the RF tag 502 following rotation of the masking element 500. In FIG. 5B, the RF tag 502 is completely covered by a portion of conductive material 504. In FIG. 5C, the RF tag 502 is partially covered by a differently shaped and sized portion of conductive material 504. As can be seen from FIGS. 5A-5C, as different, discrete portions of the RF tag 502 are covered by pieces of conductive material, the response of the RF tag 502 to an external signal can differ (for example in resonance frequency, harmonic spectra, decay characteristic, or Q factor, as described above) and thereby indicate the relative discrete rotational position of the masking element 500 and/or the RF tag 502, thereby indicating the position of the stepper motor, and thus the pressure setting of the valve. While FIGS. 5A-5C show an example of four discrete positions that can be detected, one skilled in the art will understand that additional masking elements can be used to detect additional positions.

Figure 6:
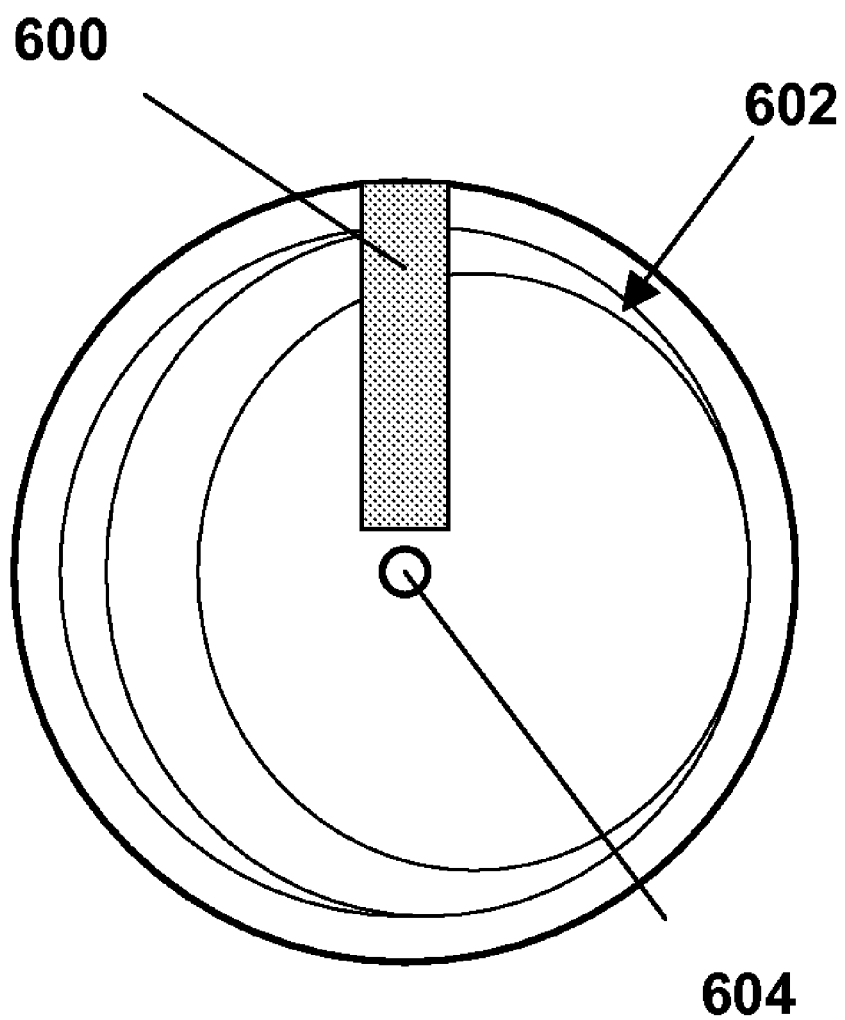
FIG. 6 is a top view of another embodiment of a radio frequency tag and a masking element.

In another embodiment, shown in FIG. 6, a masking element 600 can be in the form of a rectangle, square, or virtually any other shape, and it can be associated with an RF tag 602 having an asymmetric shape. For example, the RF tag 602 can be in the form of a disk with a rotationally asymmetric antenna pattern formed thereon. The pattern can include, for example, antenna lines with varying width, spacing, orientation, and so on. The masking element 600 can be fixed in the valve housing, while the RF tag 602 can be adapted to rotate relative to the valve housing. For example, the disk forming the RF tag 602 can be coupled to a control, e.g., in the stepper motor 120 shown in FIG. 2, so as to rotate around an axis 604 in relation to a pressure setting, as previously described. In an alternative embodiment, the RF tag 602 can be fixed within the valve and the masking element 600 can be adapted to rotate around an axis or otherwise move relative to the RF tag 602. Such rotation can cause a change or variations in the response of the RF tag 602 as the conductive masking element 600 covers different portions of the asymmetric antenna of the RF tag 602. As previously mentioned, the response can include characteristics, such as resonance frequency, harmonic spectra, decay characteristic, and/or Q factor, which can change as a result of such rotation. These characteristics can be detected in the response of the RF tag 602 to a signal emitted by a reading device.

Figure 7A:
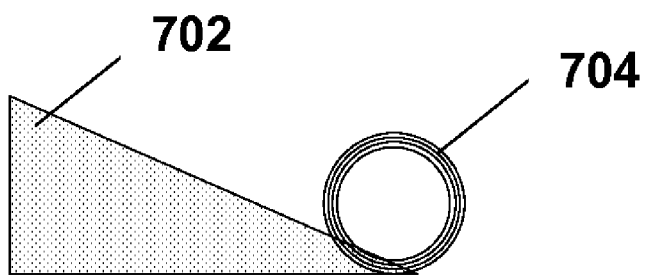
FIG. 7A is a top view of yet another embodiment of a radio frequency tag and a masking element.
Figure 7B:
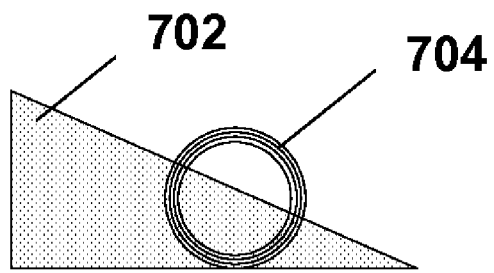
FIG. 7B is a top view the radio frequency tag and masking element shown in FIG. 7A following translation of the masking element and/or radio frequency tag.

In yet another embodiment, the masking element 126 can be configured to translate relative to the RF tag 124. For example, FIG. 7A shows a masking element 700 formed of a conductive material in the shape of a wedge which can be disposed in the valve housing adjacent to the RF tag 702. As the masking element 700 translates relative to the RF tag 702, it covers a different portion of the RF tag 702 (for example as shown in FIG. 7B), creating a detectable difference in the RF tag's response, as previously described. Such a configuration can be advantageous where a control or sensor operates linearly, such as with a sliding switch to change the flow rate of the valve. However, the translatable masking element 700 also can be coupled to a rotating control or sensor, such as a stepper motor, in a variety of ways. For example, the configuration described above in connection with FIGS. 1-3 can be adapted such that rotation of the stepper motor 120 causes translation of the masking element 700, for example via a rack and pinion gearing, pivoting arms, and so on.

Figure 8:
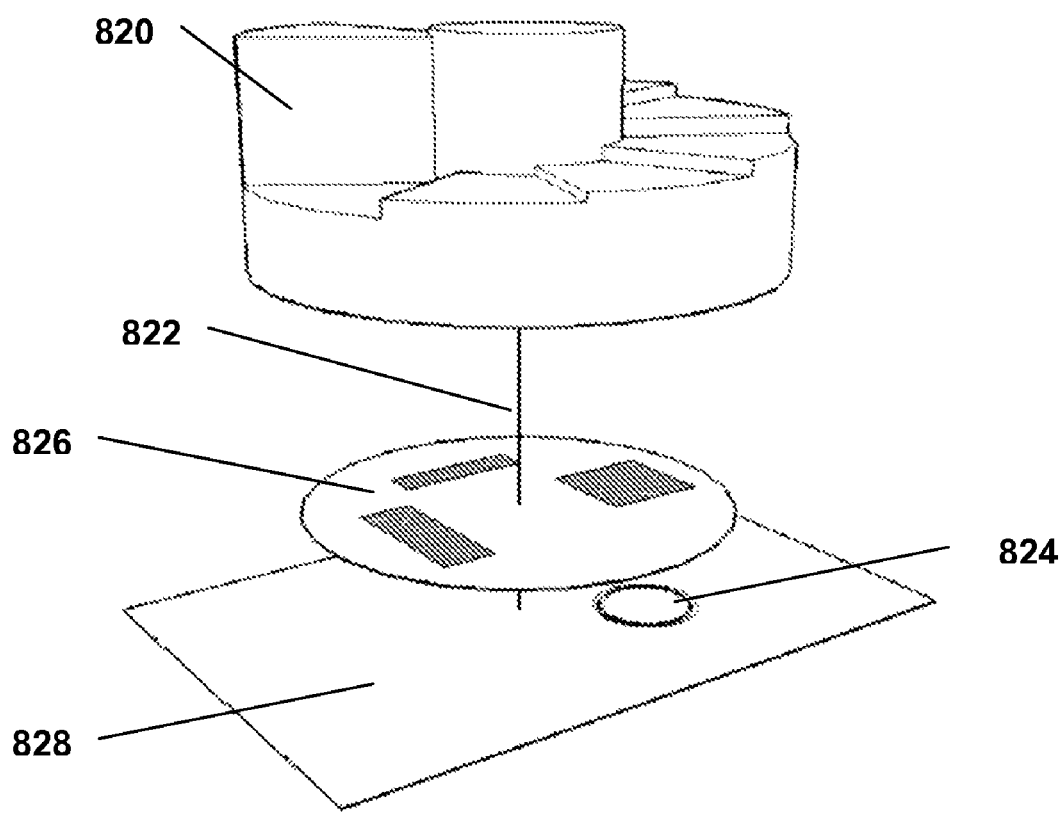
FIG. 8 is a perspective view of an exemplary embodiments of a stepper motor coupled to a masking element that is configured to at least partially cover an RF tag.

The RF tag 124 and the masking element 126 can be coupled to the stepper motor 120 in a variety of ways. For example, the stepper motor 120 can have a shaft running through its rotational axis, and the masking element 126 can be connected to this shaft such that the masking element 126 is driven by and rotates with the rotation of the stepper motor 120. Such a configuration can be advantageous for rotationally moving masking elements, as described above. FIG. 8 illustrates such a configuration and shows an exemplary embodiment of a stepper motor 820 having a shaft 822 extending therethrough and connected to a masking element 826. As shown, an RF tag 824 is attached to a surface 828, which represents the housing or other surface of an implantable valve. In other embodiments, the shaft can be attached to a gear which can drive a gear assembly that is connected to the masking element 126. In some embodiments, the gear assembly can include a rack and pinion gearing in order to drive a masking element that translates, as previously described.

As one skilled in the art will appreciate, the masking element and the RF tag can have a wide variety of other configurations, including virtually any configuration in which a masking element and an RF tag move relative to one another to indicate a setting or the position of a control. For example, in some embodiments a variety of masking element shapes can be provided, in some embodiments only one or both of the masking element and the RF tag can be configured to move relative to the other, and so on. In other embodiments, the masking element covers or is disposed in between the reading device and the RF tag. A wide variety of settings, including rotationally-determined and/or linearly determined settings, can be indicated and are not limited to stepper motors or pressure settings. The embodiments described are not meant to be limited to a particular type or category. For example, the configurations of FIGS. 4-6 can be coupled to a linearly-determined setting or control, for example via a range of known mechanical devices for transforming linear movement to rotational movement such as rack and pinion gearing, pivot arms, and so on. Also, the translatable configuration of FIGS. 7A-7B can be coupled to a rotationally-determined setting or control. Moreover, the location of the masking element and RF tag are not limited to those shown in the illustrated embodiments. The setting of the stepper motor 120, for example, can be transmitted to a location which may be particularly adapted to receive the masking element/RF tag, and/or to provide for advantageous communication properties.

Returning to FIGS. 1-3, the shape, technical specifications, and size of the RF tag 124 can vary widely. In many embodiments, a relatively small RF tag can be used so as to minimize the footprint of the tag in the device, for example with dimensions in a range of about 5 mm to 10 mm, but in other embodiments, tags with dimensions of about 3 mm to 50 mm can be used and any size is possible.

It should be understood that in many embodiments, the RF tag 124 can be chipless, and its physical/electromagnetic parameters can be used to determine position. The RF tag 124 need not have the capability to store data or to communicate according to a protocol, and need not have processing circuitry or digital logic. A chipless RF tag can provide a circuit (for example, having measurable characteristics, such as a tank circuit) and can be powered from the reading device signal. Such an RF tag can be advantageous due to its relatively low power requirements, and need not have the ability to communicate stored data or "identify" itself. However, in other embodiments the RF tag 124 can be chip-based, and can provide data storage for storing additional information related to the application. An example of chip-based tags are the commonly used RF identification tags. Some of these RF identification tags provide minimal information (such as a TRUE or FALSE value), while others can store several bytes of data. A chip-based RF tag can include processing circuitry, digital logic, a separate antenna, and/or a battery. For example, the RF tag 124 can include a memory for storing data related to the patient and/or sensor. By way of non-limiting example, the RF tag 124 can store sensed pressure data, sensor identification information (e.g., implantation date, sensor type, and sensor identifier code), sensor calibration data, historical data stored from the sensor, tag identification information (e.g., implantation date, tag type, and tag identifier code), and/or patient data (e.g., desired CSF flow rate, previous sensor measurements, and patient medical history). An external reading device, described further below, can read and/or store data in such an RF tag 124.

The RF tag 124 can have any shape, such as elliptical (including circular) or rectangular (including square), and can have virtually any size. The following table lists, by way of example only, available RF tags suitable for use with the devices and methods described herein. Passive as well as semi-passive and active tags can be used, although semi-passive and active tags sometimes are larger than passive tags because they can incorporate an internal battery, e.g., for power purposes.

| Tag Type | Frequency | | | | | |
|---|---|---|---|---|---|---|
| | 125 KHz | 5-7 MHz | 13.56 MHz | 303/433 MHz | 860-960 MHz | 2.45 GHz |
| Passive | ISO11784/5, 14223 ISO18000-2 | ISO10536 iPico DF/iPX | (ISO15693) (ISO15693) MIFARE (ISO14443) Tag-IT (ISO15693) ISO18000-3 | — | ISO18000-6 Electronic Product Code ("EPC") Class 0 EPC Class 1 EPC GEN II Intellitag tolls (Title 21) rail (Association of American Railroads ("AAR") S918) | ISO18000-4 Intellitag μ-chip |
| Semi-Passive | — | — | — | — | rail (AAR S918) Title 21 | ISO18000-4 Alien BAP |
| Active | — | — | — | Savi (American National Standards Institute ("ANSI") 371.2) ISO18000-7 RFCode | — | ISO18000-4 WhereNet (ANSI 371.1) |

By way of further explanation, one exemplary circuit for modeling an RF tag can be generally represented by a resonator circuit 900 as shown in FIG. 9A. The circuit 900 includes a capacitor 902, an inductor 904, and an intrinsic resistance 906. When the RF tag is embedded in the valve and associated with a masking element, as described above, shifts in the resonant frequency of the circuit 900 can be monitored on a continuous or intermittent basis to monitor the pressure setting through the housing 102. The resonant frequency of the circuit 900 can be detected in a variety of ways, such as by measuring power reflected from the circuit 900 or measuring decaying circulating power of the circuit 900 following a outside signal (e.g., from a reading device). FIG. 9B illustrates an example of a graph showing an output signal of the circuit 900 when introduced to an outside signal. The reflected power of the circuit 900 is at a minimum at the resonant frequency, where c) can be expressed as:

$$\omega = 2\pi f = \frac{1}{\sqrt{LC}}$$

with f representing the resonant frequency, L representing inductance of the inductor 904, and C representing capacitance of the capacitor 902. FIG. 9C illustrates another example of a graph showing an output signal of the circuit 900 when introduced to an outside signal. The reflected power of the circuit 900 in this example is at a maximum at the resonant frequency. Further examples of such RF tags and information on the use of them, including techniques for interrogating them, can be obtained from U.S. Pat. Nos. 6,025,725, and 6,278,379, and U.S. Patent Application Publication No. 2004/0134991, all of which are hereby by incorporated by reference in their entireties.

Referring again to FIGS. 1-3, the housing 102 can be formed from a variety of materials. In one exemplary embodiment, however, the housing 102 is formed from a flexible, biocompatible material. Suitable materials include, for example, polymers such as silicones, polyethylene, and polyurethanes, all of which are known in the art. The housing 102 can also optionally be formed from a radio-opaque material. A person skilled in the art will appreciate that the materials are not limited to those listed herein and that a variety of other biocompatible materials having the appropriate physical properties to enable the desired performance characteristics can be used.

As previously mentioned, the implantable valve 100 and/or the RF tag 124 and masking element 126 can also optionally include a coating 128 that is adapted to hermetically seal all or at least a portion of the RF tag 114 and/or masking element 126. The coating 128 can be applied to only a portion of the RF tag 124 and/or masking element 126 that could be exposed to fluid. The RF tag 124 and the valve 100 can be coated separately, with different coatings, or together in a single coating. An adhesive or other mating technique can optionally be used to affix the RF tag 124 and/or masking element 126 within the housing 102, however, in some embodiments it can be useful to allow the RF tag 124 and/or masking element 126 to be removed from the valve 100 if necessary. Alternatively, the valve 100 can be coated after the RF tag 124 and/or masking element 126 are disposed in the valve 100 to form a protective sheath. The valve inlet 104 and valve outlet 106 can be protected from any coating applied thereto, formed after the coating is applied, or be cleared of any coating applied thereto to allow fluid to flow therethrough. In other embodiments, only certain components of the valve 100 can be coated. A person skilled in the art will appreciate that a variety of other techniques can be used to seal the components of the valve 100.

The material used to form the coating 128 can vary, and a variety of techniques can be used to apply the coating. By way of non-limiting example, suitable materials include polyurethane, silicone, solvent-based polymer solutions, and any other polymer that will adhere to the components to which it is applied to, and suitable techniques for applying the coating include spray-coating or dip-coating.

Figure 10A:
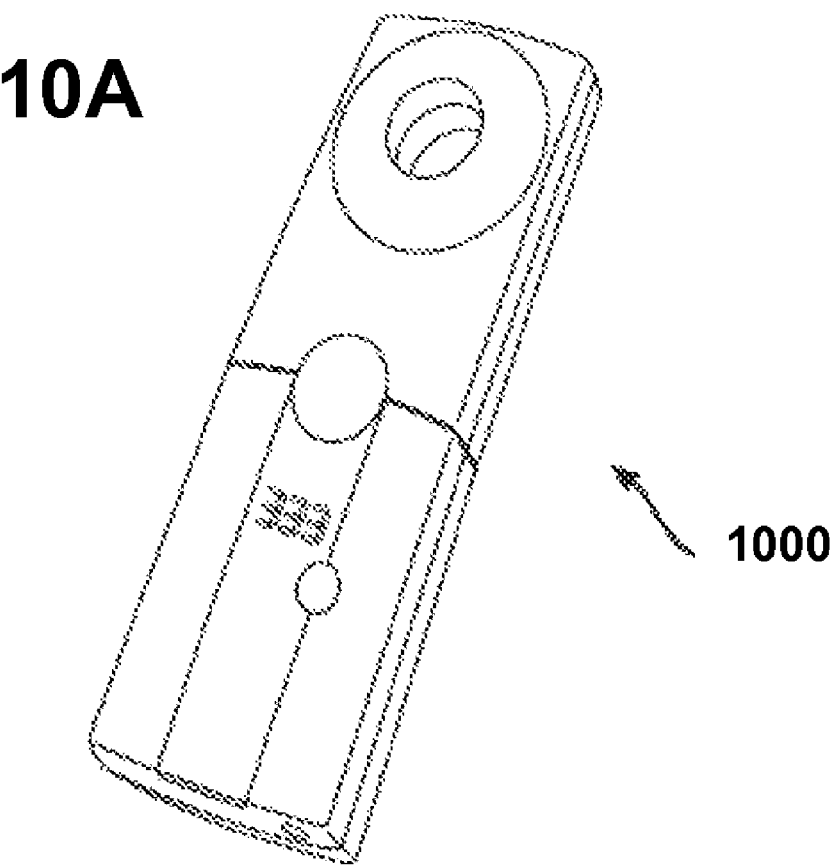
FIG. 10A is a perspective view of one exemplary reading device for reading a pressure setting from a valve having a radio frequency tag and masking element.
Figure 10B:
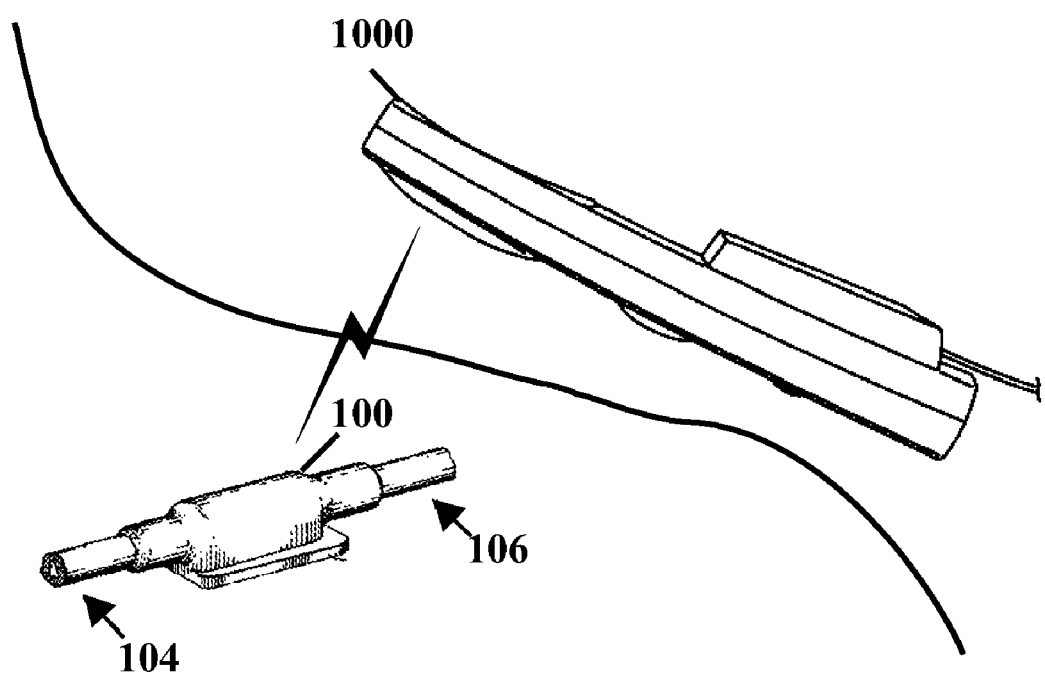
FIG. 10B illustrates the valve of FIG. 1 implanted in a body and being read by the reading device shown in FIG. 10A.

FIG. 10A shows one exemplary embodiment of a reading device 1000, such as an RF telemetry device, for use in obtaining information from the RF tag 124. The reading device 1000 can emit a signal at one frequency or over a range of frequencies, and can listen for the response thereto, e.g., from the RF tag 124. In the case of a chipless RF tag, a characteristic of the response from the tag can indicate a measured flow rate, as explained previously. In the case of a chip-based RF tag having memory associated therewith, the response of the tag can indicate the pressure setting in the same way as previously described for a chipless tag, and it can also communicate (e.g., according to a communication protocol) additional information stored in its memory for the reading device. Any type of external reading device can be used. In one exemplary embodiment, the reading device 1000 can include an RF module (e.g., transmitter and receiver), a control unit (e.g., microcontroller), a coupling element to the transponder (e.g., antenna), and an interface (e.g., Recommended Standard (RS) 232, RS-485, Firewire, Universal Serial Bus (USB), Bluetooth, ZigBee, etc.) to enable communication with another device (e.g., a personal computer). The reading device 1000 can provide the power required by the RF tag 124 to operate, e.g., via inductive coupling. As shown in FIG. 10B, the reading device 1000 can be positioned in proximity to an implanted valve 100 to telemetrically communicate with the RF tag 124, and thereby obtain a reading indicative of a pressure setting.

Figure 11:
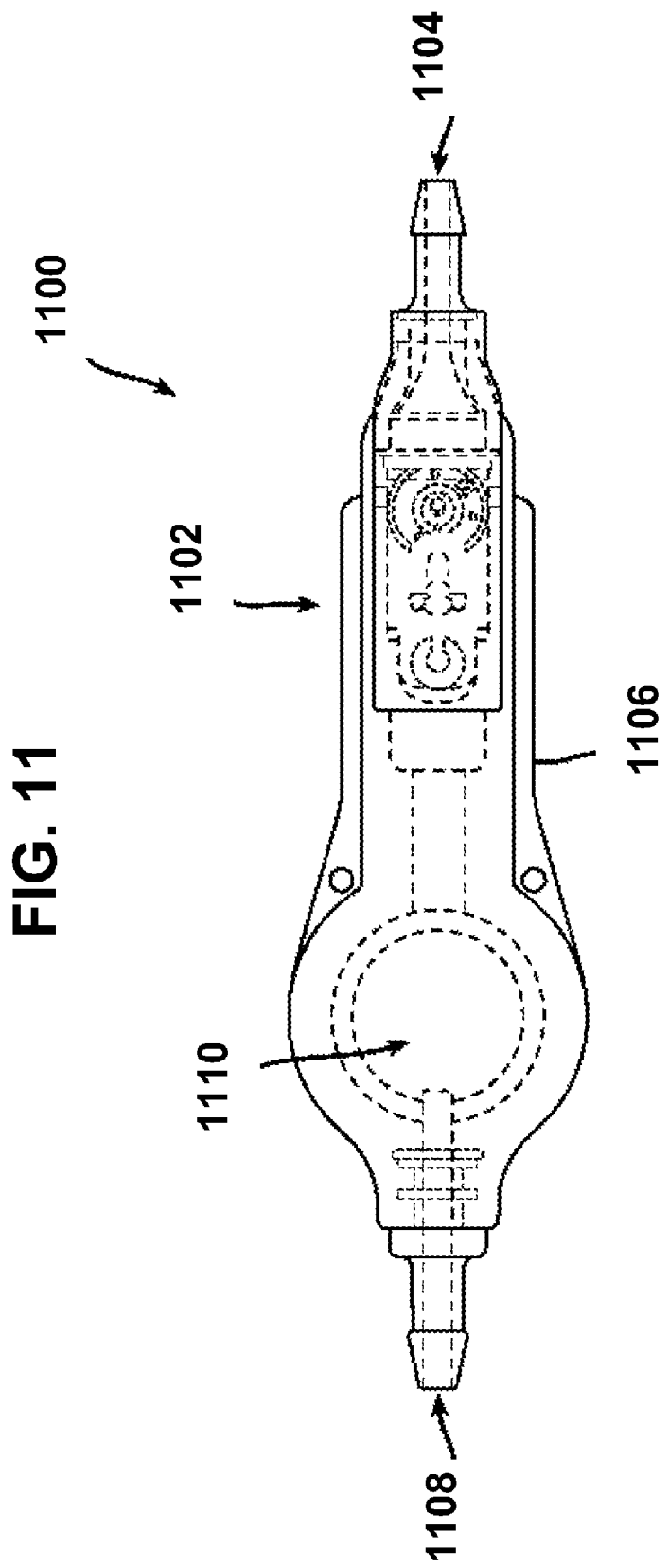
FIG. 11 is a top view of another embodiment of an implantable valve suitable for use in a hydrocephalus shunt.

FIG. 11 illustrates another exemplary embodiment of an implantable valve for a hydrocephalus shunt which can have a pressure setting indicator. As shown, the implantable valve 1100 can include a valve housing 1106 for receiving fluid flow (such as CSF) therethrough between an inlet port 1108 and an outlet port 1104. A reservoir 1110 can be provided for housing a pressure sensor or a flow sensor, or other sensors and/or controls. For example, suitable pressure sensors are described in co-pending, commonly assigned U.S. patent application Ser. No. 10/907,665, entitled "Pressure Sensing Valve" by Mauge et al., filed Apr. 11, 2005 and now published as U.S. Publication No. 2006-0211946 A1, and in U.S. Pat. Nos. 5,321,989, 5,431,057, and EP Patent No. 1 312 302, the teachings of all of which are hereby incorporated by reference in their entireties. Suitable flow sensors are described in co-pending, commonly assigned U.S. patent application Ser. No. 11/931,127, entitled "Wireless Flow Sensor" by Salim Kassem and Aaron Gilletti and published as U.S. Publication No. 2009/0107233 and filed on even date herewith. The implantable valve 1100 can also include a valve assembly 1102 for controlling the flow of fluid through the valve 1100 according to remotely or telemetrically selectable settings. For example, the valve assembly can include a stepper motor, such as was described in connection with FIG. 1. A coating can be disposed over the valve 1100. Further information on implantable valves can be obtained from U.S. Publication No. 2006-0211946 A1, referenced above. Implantable valve 1100 can include a masking element and/or RF tag to indicate the pressure setting of valve assembly 1102 according to any of the previously-described embodiments.

In another aspect, a method is provided for non-invasively determining the position or setting of a mechanical device, such as a control or sensor in an implanted medical device, and for indicating that information to another device. In one embodiment, an exemplary method can include implanting a valve, such as the valve 100 described above in connection with FIGS. 1-3, in a body. In the case of a hydrocephalus shunt, a hydrocephalus valve can be subcutaneously implanted in a patient, as shown in FIG. 10B. It should be understood that while FIG. 10B shows the implantation of a valve in a shoulder region, the device can be implanted virtually anywhere, for example subcutaneously behind the ear, or on the head, torso, etc. The method can also include coupling a proximal end of a catheter, such as a ventricular catheter, to an inlet port of the flow sensor. Another catheter, such as a drainage catheter, can be coupled to an outlet port of the flow sensor. The drainage catheter can extend through the patient to an area where excess fluid, e.g., CSF, can drain safely.

The method can further include wirelessly transmitting a wireless signal to an RF tag embedded in the valve, for example using a reading device such as reading device 1000 described above in connection with FIG. 10A. The transmitted signal can include one or more frequencies, for example radio frequencies. In some embodiments, the wireless signal can be transmitted according to a protocol to communicate with an RF tag having a chip therein. The method can also include receiving a response from the RF tag that indicates a pressure setting of the valve. The response can be a radio frequency response and can have one or more characteristics, such as resonance frequency, harmonic spectra, decay characteristics, and Q factor, that can be detected and analyzed in order to determine the current pressure setting of the valve. The determination of the pressure setting can be performed using calibration data for a particular pressure sensor and/or valve. In some embodiments, the calibration data, as well as other data such as historical data, can be transmitted from an RF tag having a memory to the reading device. The method can further include changing the pressure setting of the valve. In some embodiments, this can be performed using a programming device that produces and directs a changing electromagnetic field to a stepper motor. Another signal can be wirelessly transmitted to the RF tag using a reading device, and the response to the signal can be analyzed to indicate the changed pressure setting.

Further information on wireless shunts can be obtained from U.S. patent application Ser. No. 11/931,127, entitled "Wireless Flow Sensor" by Salim Kassem and published as U.S. Publication No. 2009/0107233, U.S. patent application Ser. No. 11/931,151, entitled "Wireless Pressure Sensing Shunts" by Salim Kassem and published as U.S. Publication No. 2009/0112103, and U.S. patent application Ser. No. 11/931,187, entitled "Wireless Shunts With Storage" by Salim Kassem and published as U.S. Publication No. 2009/0112308, all of which were filed on the same date as the present application and which are hereby incorporated by reference in their entirety. Also incorporated by reference in its entirety is co-pending, commonly assigned U.S. patent application Ser. No. 10/907,665, entitled "Pressure Sensing Valve" and published as U.S. Publication No. 2006-0211946 A1.

A person skilled in the art will appreciate that the various methods and devices disclosed herein can be formed from a variety of materials. Moreover, particular components can be implantable and in such embodiments the components can be formed from various biocompatible materials known in the art. Exemplary biocompatible materials include, by way of non-limiting example, composite plastic materials, biocompatible metals and alloys such as stainless steel, titanium, titanium alloys and cobalt-chromium alloys, glass, and any other material that is biologically compatible and non-toxic to the human body.

One skilled in the art will appreciate further features and advantages based on the above-described embodiments. Accordingly, the disclosure is not to be limited by what has been particularly shown and described, except as indicated by the appended claims. All publications and references cited herein are expressly incorporated herein by reference in their entirety.

What is claimed is:

1. An implantable valve, comprising:
   a valve housing adapted to receive fluid flow therethrough between a valve inlet and a valve outlet;
   a valve assembly disposed within the valve housing and having a plurality of predetermined pressure settings for controlling a rate of fluid flowing through the valve housing;
   a radio frequency tag disposed in the valve housing and adapted to interact with a wireless signal to produce a response thereto; and
   a masking element disposed in the valve housing, at least one of the masking element and the radio frequency tag being configured to rotate in a circular motion relative to the other one of the masking element and the radio frequency tag such that the masking element masks different portions of the radio frequency tag when the masking element and the radio frequency tag are in different rotational positions relative to one another to alter the response of the radio frequency tag and thereby indicate a pressure setting of the valve assembly.

2. The implantable valve of claim 1, wherein the masking element comprises a conductive member that alters the response of the radio frequency tag.

3. The implantable valve of claim 1, wherein at least one characteristic of the response indicates the pressure setting of the valve assembly, the at least one characteristic being selected from the group consisting of resonant frequency, harmonic spectra, decay characteristic, and Q factor.

4. The implantable valve of claim 1, wherein the valve assembly comprises an adjustment mechanism configured to rotate around an axis thereof to select one of the plurality of pressure settings and to effect rotation of the masking element.

5. The implantable valve of claim 1, wherein the masking element comprises a disk formed at least in part of a conductive material and configured to rotate in the circular motion around an axis thereof such that the conductive material selectively masks at least part of the radio frequency tag.

6. The implantable valve of claim 5, wherein the conductive material is selected from the group consisting of a spiral and a plurality of discrete conductive sections.

7. The implantable valve of claim 1, wherein the radio frequency tag includes a chip for storing data and an antenna adapted to communicate the stored data to an external reading device.

8. The implantable valve of claim 1, wherein the valve assembly comprises a movable adjustment mechanism adapted to select one of the plurality of pressure settings in response to a magnetic field created by an external control device.

9. The implantable valve of claim 1, wherein the wireless signal is emitted from an external reading device.

10. The implantable valve of claim 1, wherein the radio frequency tag is configured to rotate in a circular motion relative to the masking element while the masking element remains fixed.

11. An implantable valve, comprising:
    a valve housing adapted to receive fluid flow therethrough between a valve inlet and a valve outlet;
    a valve assembly disposed within the valve housing and having a plurality of selectable positions that each allow fluid to flow through the valve assembly at different pressure settings;
    a radio frequency tag disposed in the valve housing and adapted to interact with a wireless signal to produce a response thereto; and
    a masking element disposed in the valve housing, at least one of the masking element and the radio frequency tag is configured to rotate relative to the other one of the masking element and the radio frequency tag such that different portions of the radio frequency tag are covered by the masking element when the masking element and the radio frequency tag are in different rotational positions relative to one another to alter the response of the radio frequency tag and thereby indicate the selected position of the valve assembly.

12. The implantable valve of claim 1, wherein each of the predetermined pressure settings corresponds to one of a plurality of predetermined pressure settings at which fluid flows through the valve assembly, the response of the radio frequency tag indicating the corresponding predetermined pressure setting.

13. The implantable valve of claim 1, wherein the masking element is configured to rotate in a circular motion relative to the radio frequency tag while the radio frequency tag remains fixed.

14. The implantable valve of claim 1, wherein the masking element and the radio frequency tag are each configured to rotate in a circular motion relative to the valve housing.

15. The implantable valve of claim 1, wherein the masking element comprises a non-conductive material having a plurality of discrete conductive portions disposed on the non-conductive material.

16. The implantable valve of claim 15, wherein at least one of the discrete conductive portions has a surface area configured to mask a first portion of the radio frequency tag when the masking element and the radio frequency tag are in a first rotational position relative to one another, and at least one of the discrete conductive portions has a different surface area configured to mask a second, different portion of the radio frequency tag when the masking element and the radio frequency tag are in a second, different rotational position relative to one another.

17. The implantable valve of claim 16, wherein the first portion includes an entirety of the radio frequency tag, and the second portion includes a partial area of the radio frequency tag.

18. The implantable valve of claim 11, wherein the masking element comprises a non-conductive material and a plurality of discrete portions of conductive material, the relative position of the radio frequency tag relative to the discrete portions of conductive material determining the response of the radio frequency tag.

19. The implantable valve of claim 11, wherein the at least one of the masking element and the radio frequency tag is configured to rotate 360° relative to the other one of the masking element and the radio frequency tag.

* * * * *